US010649541B2

(12) United States Patent
Tanenbaum et al.

(10) Patent No.: US 10,649,541 B2
(45) Date of Patent: May 12, 2020

(54) KEYBOARD FOR A MEDICAL TREATMENT SYSTEM

(71) Applicant: Fresenius Medical Care Holdings, Inc., Waltham, MA (US)

(72) Inventors: Lee Daniel Tanenbaum, Walnut Creek, CA (US); Aleo Nobel Mok, Orinda, CA (US); Matin Vareth, Clayton, CA (US); Alexander Joseph Brown, Danville, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1605 days.

(21) Appl. No.: 14/497,532

(22) Filed: Sep. 26, 2014

(65) Prior Publication Data

US 2016/0091984 A1    Mar. 31, 2016

(51) Int. Cl.
*G06F 3/02* (2006.01)
*A61M 1/14* (2006.01)
*G06F 1/16* (2006.01)

(52) U.S. Cl.
CPC ............ *G06F 3/0208* (2013.01); *A61M 1/14* (2013.01); *G06F 1/1667* (2013.01); *A61M 2205/502* (2013.01); *A61M 2209/08* (2013.01)

(58) Field of Classification Search
CPC . A61M 1/14; A61M 2205/502; G06F 1/1667; G06F 3/0208
See application file for complete search history.

(56) References Cited

U.S. PATENT DOCUMENTS

| | | | |
|---|---|---|---|
| 6,700,774 B2 * | 3/2004 | Chien | G06F 1/1616 361/679.2 |
| D607,564 S | 1/2010 | Crnkovich | |
| 2004/0012918 A1 * | 1/2004 | Chen | G06F 1/1616 361/679.11 |
| 2010/0134964 A1 * | 6/2010 | Smith | B60R 11/0252 361/679.2 |

OTHER PUBLICATIONS

2008T Hemodialysis Machine Operator's Manual, Fresenius Medical Care, P.N. 490122 Rev. E, Copyright 2008-2010.

* cited by examiner

*Primary Examiner* — Pranav N Patel
(74) *Attorney, Agent, or Firm* — Fish & Richardson P.C.

(57) ABSTRACT

A medical treatment system comprising a housing; a recess defined by the housing; and a keyboard connected to the housing by a mechanism configured to permit the keyboard to move between: a deployed position in which the keyboard is disposed outside of the recess at an angle of 10° to 80° relative to a front surface of the housing; and a stored position in which the keyboard is at least partially disposed in the recess and keys of the keyboard are exposed for use by a user.

13 Claims, 13 Drawing Sheets

KEYBOARD FOR A MEDICAL TREATMENT SYSTEM

TECHNICAL FIELD

This disclosure relates to a keyboard for a medical treatment system.

BACKGROUND

Dialysis is a treatment used to support a patient with insufficient renal function. Dialysis machines typically include input devices that can be used by nurses or doctors to input information related to treatment into the dialysis machine.

SUMMARY

In one aspect, a medical treatment system includes a housing, a recess defined by the housing, and a keyboard connected to the housing by a mechanism. The mechanism is configured to permit the keyboard to move between a deployed position and a stored position. The keyboard is disposed outside of the recess at an angle of 10° to 80° relative to a front surface of the housing when the keyboard is in the deployed position. The keyboard is at least partially disposed in the recess and keys of the keyboard are exposed for use by a user when the keyboard is in the stored position.

Implementations can include one or more of the following features.

In some implementations, the medical treatment system is a hemodialysis system that includes a hemodialysis machine.

In some implementations, the keyboard is in a substantially vertical position when the keyboard is disposed in the recess.

In some implementations, the medical treatment system also includes a blood pump. The blood pump is disposed on the front surface of the housing beneath the keyboard.

In some implementations, a bottom end of the keyboard is positioned further away from the front surface of the housing than the blood pump when the keyboard is in the deployed position.

In some implementations, the mechanism includes a track disposed on the housing within the recess. The track includes a sliding element for moving along the track. The mechanism also includes a link having a first end that is affixed to the sliding element of the track. A top end of the keyboard is affixed to a second end of the link such that the keyboard can move along the track in relation to the sliding element.

In some implementations, the medical treatment system also includes a support member that is affixed to an undersurface of the keyboard. The support member makes contact with the medical treatment machine to retain the keyboard at the angle of 10° to 80° relative to the front surface of the housing when the keyboard is in the deployed position.

In some implementations, the dimensions of the support member result in the keyboard being disposed at an angle of 30° to 60° relative to the front surface of the housing when the keyboard is in the deployed position.

In some implementations, the support member is a wedge.

In some implementations the medical treatment system also includes a protrusion that is affixed to the housing adjacent the recess. The protrusion retains the keyboard within the recess when the keyboard in the stored position.

In some implementations, a bottom end of the keyboard is positioned below a horizontal plane that extends from the most vertical point of the blood pump when the keyboard is in the deployed position.

In some implementations, the medical treatment system also includes a hinge. The hinge has a first end that is affixed to the housing. A top end of the keyboard is affixed to a second end of the hinge. The medical treatment system also includes a leg having a first end that is pivotably affixed to an undersurface of the keyboard. A second end of the leg makes contact with a surface within the recess when the keyboard is in the deployed position and the leg is in an extended position.

In some implementations, the keyboard is disposed at an angle of 30° to 60° relative to the front surface of the housing when the keyboard is in the deployed position and the leg is in the extended position.

In some implementations, the keyboard is disposed outside of the recess at an angle of between 30° and 60° relative to the front surface of the housing when the keyboard is in the deployed position.

In another aspect, a method includes entering information into a medical treatment system via a keyboard that is in a deployed position. The keyboard is disposed at an angle of 10° to 80° relative to a front surface of a housing of the medical treatment system when the keyboard is in the deployed position. The method also includes positioning the keyboard into a stored position. The keyboard is at least partially disposed in a recess defined by the housing when the keyboard is in the stored position. Keys of the keyboard are exposed for use when the keyboard is in the stored position. The method also includes, during administration of medical treatment, entering information into the medical treatment system via the keyboard while the keyboard is in the stored position.

Implementations can include one or more of the following features.

In some implementations, the medical treatment system is a hemodialysis system that includes a hemodialysis machine.

In some implementations, the information includes one or more patient parameters.

In some implementations, the information includes one or more treatment parameters.

In some implementations, the treatment parameters include an ultrafiltration rate.

In some implementations, the keyboard is positioned at an angle of between 30° and 60° relative to the front surface of the housing when the keyboard is in the deployed position.

In some implementations, the keyboard is in a substantially vertical position when the keyboard is in the stored position.

Implementations can include one or more of the following advantages.

In some implementations, the keyboard can be placed in a stored position during medical treatment, and the keyboard can be placed in a deployed position before or after medical treatment. Medical personnel typically use the keyboard the most before and after medical treatment to input patient parameters and medical treatment information. When the keyboard is in the deployed position, the keyboard is positioned at an angle relative to the front surface of the housing of the medical treatment machine that is appropriate for typing comfortably.

In some implementations, during medical treatment, the keyboard can be stored in the recess of the housing so that the keyboard does not obstruct components of the medical treatment machine from view. In the stored position, the keys of the keyboard are exposed. As such, even when the keyboard is stored, medical personnel may access the keyboard to input patient parameters or medical treatment information.

In some implementations, the keyboard can be easily moved from the stored position to the deployed position and vice versa. As such, medical personnel will be more likely to place the keyboard in the stored position during treatment so that the components on the front of the medical treatment machine are not obstructed from view. Also, medical personnel will be more likely to place the keyboard in the deployed position for significant data entry.

Other aspects, features, and advantages of the invention will be apparent from the description and drawings, and from the claims.

DETAILED DESCRIPTION

Figure 1:
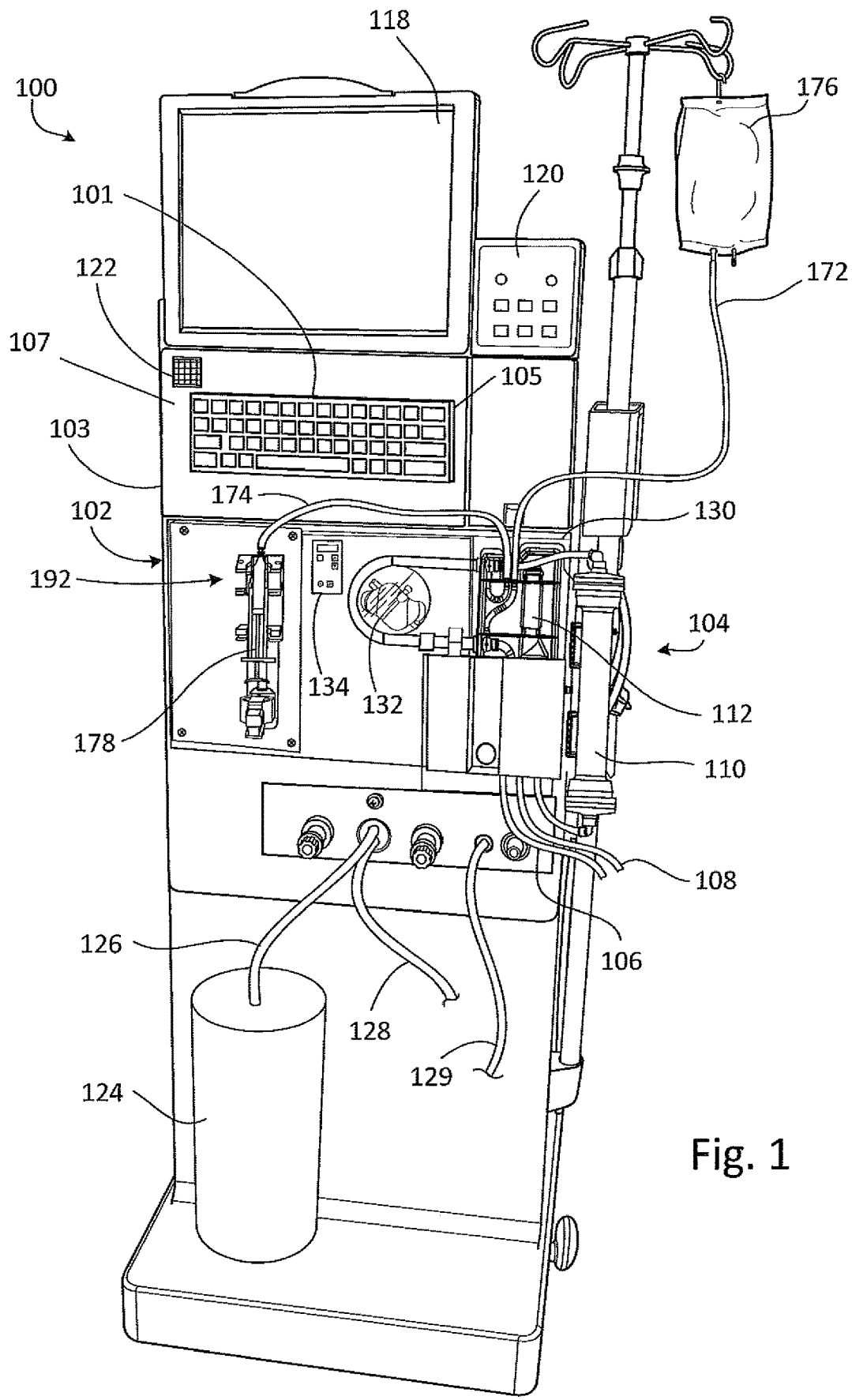
FIG. 1 is a front perspective view of a hemodialysis system, including a retractable keyboard.

At various points before, during, or after hemodialysis treatment, medical personnel may need to input information into a hemodialysis machine. For example, before treatment, a nurse may input patient parameters, such as a Patient ID. The nurse may also input medical treatment information, such as information related to the patient's treatment prescription. The information related to the patient's treatment prescription can include dialysate parameters and a concentrate selection. There is typically a large amount of information that must be input into the hemodialysis machine before treatment begins.

The hemodialysis machines described herein include a keyboard for inputting such information. Before treatment, the keyboard can assume a deployed position. The keyboard can extend out from the hemodialysis machine and be positioned at a height and an angle relative to a front surface of the housing of the hemodialysis machine that is appropriate for typing comfortably. In other words, the keyboard can be positioned relative to the nurse in a way similar to how a keyboard is typically positioned relative to a person who is using a computer.

During treatment, the nurse may also need to input information into the hemodialysis machine. For example, the nurse may need to adjust treatment parameters for the hemodialysis machine for various reasons. The amount of information that must be input into the hemodialysis machine during treatment is typically not as large as the amount of information that must be input before treatment begins. During treatment, it is beneficial for the various components of the hemodialysis machine to remain in full view of the nurse. When the keyboard extends out from the hemodialysis machine in the deployed position, as described above, the keyboard may obstruct some portions of the hemodialysis machine (e.g., portions of the hemodialysis machine that are disposed beneath the keyboard, such as a blood pump, blood lines, and dialysate lines) from the nurse's view. To prevent such a scenario, before treatment begins, the nurse can move the keyboard into a stored position in which the keyboard is at least partially disposed in a recess defined by the housing of the hemodialysis machine. While in the stored position, keys of the keyboard are exposed for use by the nurse. As such, while the keyboard may not be optimally positioned for extended typing, the nurse is able to input information into the hemodialysis machine during treatment via the keyboard without having her view of the hemodialysis machine obstructed by the keyboard.

Once treatment has concluded, and it is not as essential for the nurse to have complete view of the entire hemodialysis machine, the nurse can move the keyboard back into the deployed position for more comfortable typing. Alternatively, the nurse can leave the keyboard in the stored position after treatment while disconnecting the patient from the hemodialysis machine and completing post-treatment functions in order to keep sight of the potentially hidden portions of the hemodialysis machine.

Referring to FIG. 1, a hemodialysis system 100 includes a hemodialysis machine 102 to which a disposable blood component set 104 that forms a blood circuit is connected. During hemodialysis, arterial and venous patient lines 106, 108 of the blood component set 104 are connected to a patient and blood is circulated through various blood lines and components, including a dialyzer 110, of the blood component set 104. At the same time, dialysate is circulated through a dialysate circuit formed by the dialyzer 110 and various other dialysate components and dialysate lines connected to the hemodialysis machine 102. Many of these dialysate components and dialysate lines are located inside the housing 103 of the hemodialysis machine 102, and are thus not visible in FIG. 1. The dialysate passes through the dialyzer 110 along with the blood. The blood and dialysate passing through the dialyzer 110 are separated from one another by a semi-permeable structure (e.g., a semi-permeable membrane and/or semi-permeable microtubes) of the dialyzer 110. As a result of this arrangement, toxins are removed from the patient's blood and collected in the dialysate. The filtered blood exiting the dialyzer 110 is returned to the patient. The dialysate that exits the dialyzer 110 includes toxins removed from the blood and is commonly referred to as "spent dialysate." The spent dialysate is routed from the dialyzer 110 to a drain.

One of the components of the blood component set 104 is an air release device 112. The air release device 112 includes a self-sealing vent assembly that allows air to pass therethrough while inhibiting (e.g., preventing) liquid from passing therethrough. As a result, if blood passing through the blood circuit during treatment contains air, the air will be vented to atmosphere as the blood passes through the air release device 112.

As shown in FIG. 1, a dialysate container 124 is connected to the hemodialysis machine 102 via a dialysate supply line 126. A drain line 128 and an ultrafiltration line 129 also extend from the hemodialysis machine 102. The dialysate supply line 126, the drain line 128, and the ultrafiltration line 129 are fluidly connected to the various dialysate components and dialysate lines inside the housing 103 of the hemodialysis machine 102 that form part of the dialysate circuit. During hemodialysis, the dialysate supply line 126 carries fresh dialysate from the dialysate container 124 to the portion of the dialysate circuit located inside the hemodialysis machine 102. As noted above, the fresh dialysate is circulated through various dialysate lines and dialysate components, including the dialyzer 110, that form the dialysate circuit. As the dialysate passes through the dialyzer 110, it collects toxins from the patient's blood. The resulting spent dialysate is carried from the dialysate circuit to a drain via the drain line 128. When ultrafiltration is performed during treatment, a combination of the spent dialysate and excess fluid drawn from the patient is carried to the drain via the ultrafiltration line 129.

The blood component set 104 is secured to a module 130 attached to the front of the hemodialysis machine 102. The module 130 includes a blood pump 132 capable of driving blood through the blood circuit. The module 130 also includes various other instruments capable of monitoring the blood flowing through the blood circuit. The module 130 includes a door that when closed, as shown in FIG. 1, cooperates with the front face of the module 130 to form a compartment sized and shaped to receive the blood component set 104. In the closed position, the door presses certain blood components of the blood component set 104 against corresponding instruments exposed on the front face of the module 130. As will be described in greater detail below, this arrangement facilitates control of the flow of blood through the blood circuit and monitoring of the blood flowing through the blood circuit.

The blood pump 132 can be controlled by a blood pump module 134. The blood pump module 134 includes a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in an arterial drip chamber.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

Still referring to FIG. 1, the hemodialysis machine 102 includes a keyboard 101, a touch screen 118 and a control panel 120. The keyboard 101, the touch screen 118, and the control panel 120 allow the operator to input various different treatment parameters to the hemodialysis machine 102 and to otherwise control the hemodialysis machine 102. In addition, the touch screen 118 serves as a display to convey information to the operator of the hemodialysis system 100. A speaker 122 is positioned below the touch screen 118 and functions to provide audio signals to the operator of the system 100. Thus, the hemodialysis machine 102 is capable of providing both visual alerts via the touch screen 118 and audio alerts via the speaker 122 to the operator of the system 100 during use.

Figure 2A:
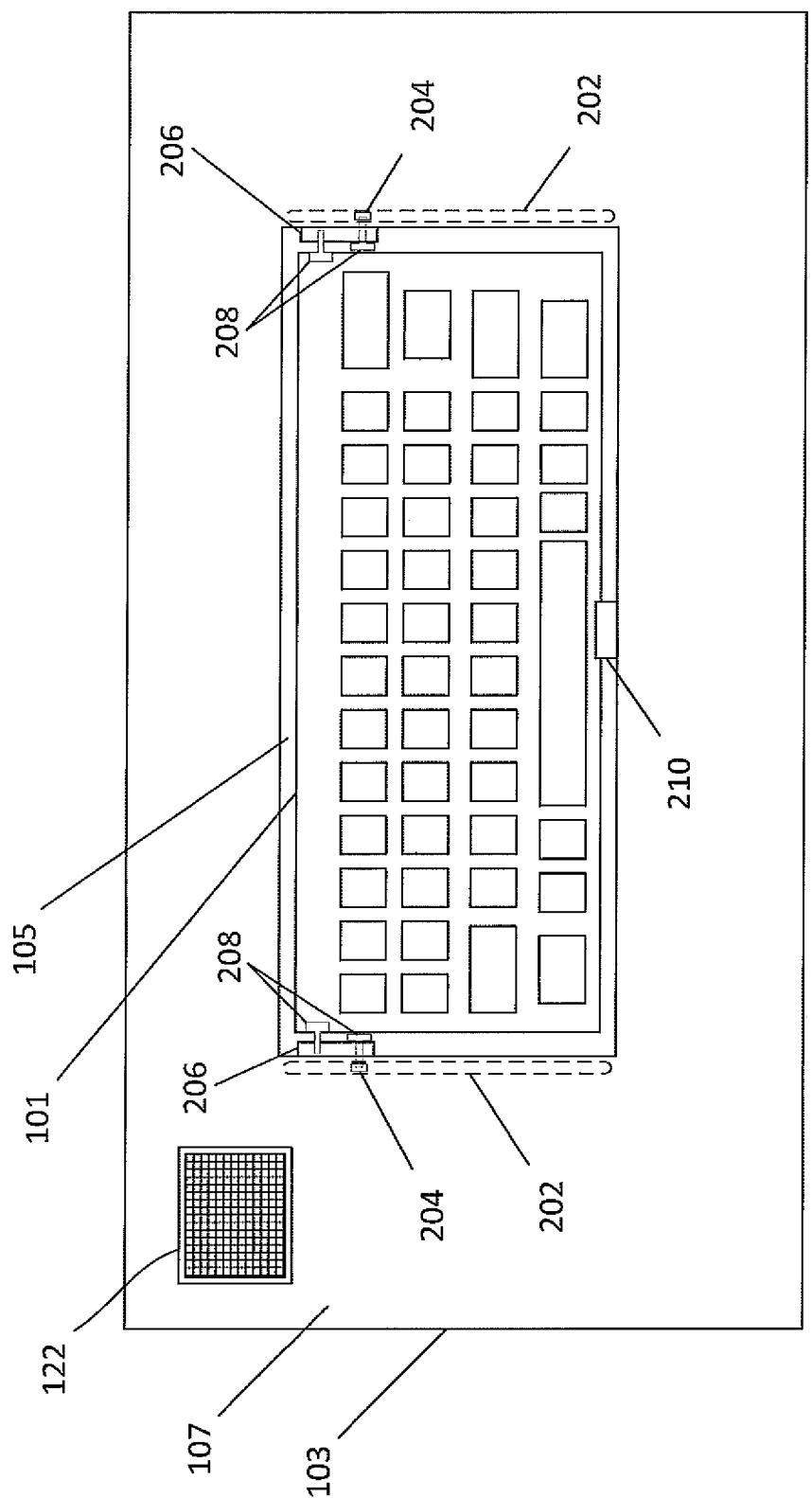
FIG. 2a is a front view of the keyboard of the hemodialysis system of FIG. 1 in a stored position.
Figure 2B:
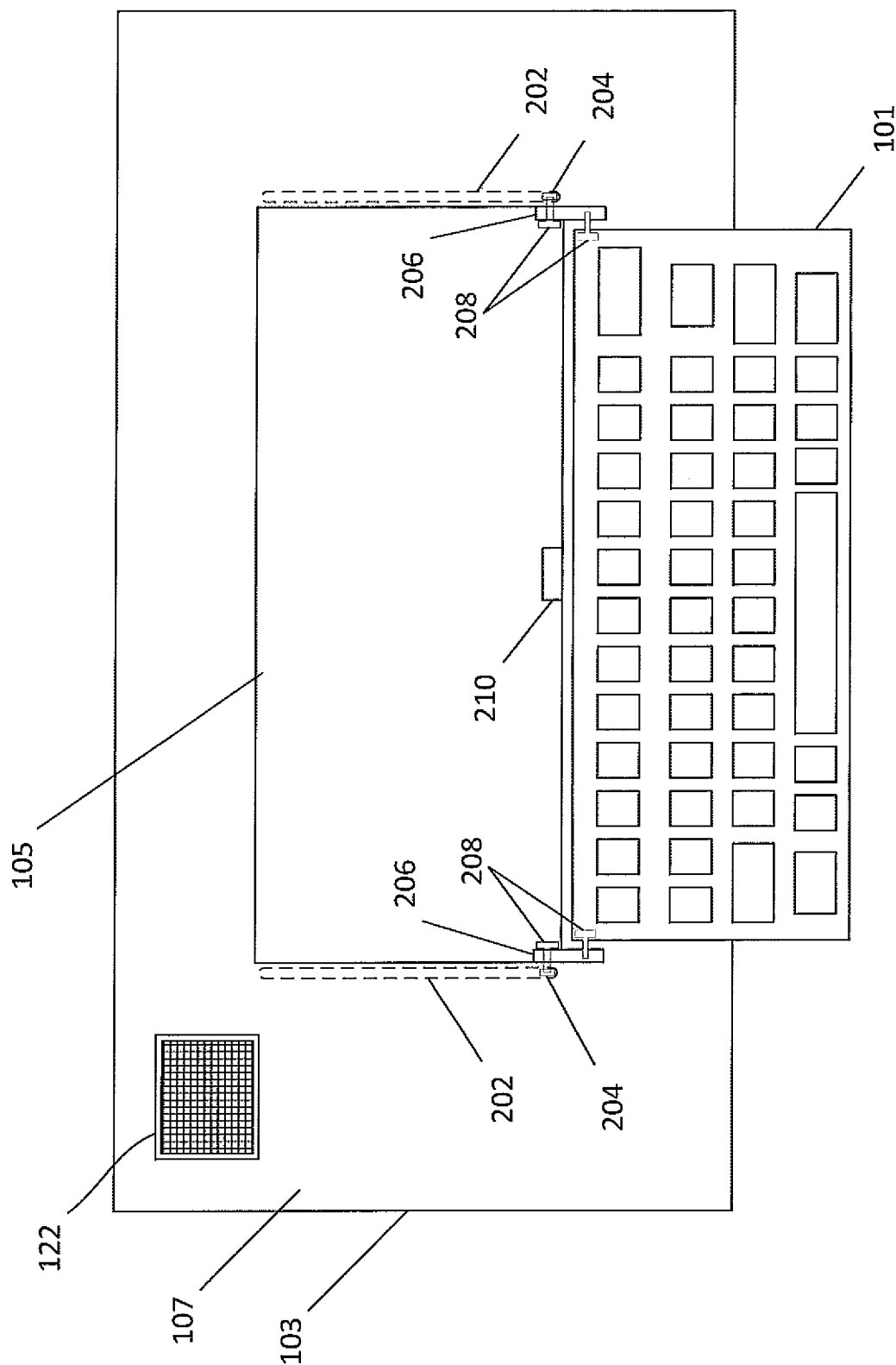
FIG. 2b is a front view of the keyboard of the hemodialysis system of FIG. 1 in a deployed position.

As shown in FIGS. 1, 2a, and 2b, the keyboard 101 is positioned in a recess 105 defined by the housing 103 of the hemodialysis machine 102. The housing 103 has a front surface 107. When the keyboard 101 is in a stored position in the recess 105, the keyboard 101 is at least partially disposed in the recess 105 and keys of the keyboard 101 are exposed for use by a user. When in the stored position, the keyboard 101 is in a substantially vertical position. The keyboard 101 can also assume other positions, as described in more detail below.

FIG. 2a shows a front view of a portion of the hemodialysis machine 102. The keyboard 101 is positioned in the recess 105 in the housing 103 of the hemodialysis machine 102. The keyboard 101 is connected to the housing 103 by a mechanism configured to permit the keyboard 101 to move between the stored position and a deployed position.

Two tracks 202 are disposed on the housing 103. The tracks 202 are obstructed from view by a front surface 107 of the housing 103. Each track 202 is disposed on the housing 103, adjacent to one of the sides of the recess 105. Each track 202 includes a sliding element 204 that can move along the track 202. Each sliding element 204 is affixed to a first end of a link 206 by a fastener 208, and a second end of the link 206 is affixed to a top end of the keyboard 101 by a fastener 208. The fasteners 208 are typically bolts that protrude through holes in the links 206 that are lined with bushings, thereby allowing the links 208 to pivot about each fastener 208. In FIG. 2a, some of the fasteners 208 are partially obstructed from view. A protrusion 210 affixed to the housing 103 extends upwardly and overlaps the recess 105 to retain the keyboard 101 within the recess when the keyboard 101 is in the stored position.

The tracks 202, sliding elements 204, and links 206 allow the keyboard 101 to move along the tracks 202 in relation to the sliding elements 204 to assume other positions. The keyboard 101 can move between at least two fixed positions. FIG. 2a shows the keyboard 101 in a stored position in which the keyboard is at least partially disposed in the recess. While in the stored position, keys of the keyboard 101 are exposed for use by a user. This allows the user to input data into the hemodialysis machine 102 using the keyboard 101, even when the keyboard is in the stored position during treatment.

FIG. 2b shows a front view of a portion of the hemodialysis machine 102 with the keyboard 101 in a deployed position. When the keyboard 101 is in the deployed position, the keyboard 101 is disposed outside of the recess 105 at a particular angle relative to the front surface 107 of the housing 103. Because FIG. 2b is a front view of the hemodialysis machine 102, the angle at which the keyboard 101 is positioned is not visually apparent. A support member or wedge 304 (shown in FIGS. 3a-3d) props the keyboard 101 against the housing 103 to maintain the keyboard 101 in the deployed position. The angle at which the keyboard 101 extends with respect to the dialysis machine 102 when the keyboard 101 is in the deployed position can be selected to allow the user to comfortably input data using the keyboard 101. This can be particularly beneficial during set up for treatment, which often times requires significant amounts of data to be input via the keyboard 101.

The housing 103 of the hemodialysis machine 102 also defines a second recess 308 (shown in FIGS. 3a-3d) that extends inwardly (i.e., toward the inside of the hemodialysis machine 102) from the recess 105. The wedge 304 is at least partially disposed in the second recess 308 when the keyboard 101 is in the stored position of FIGS. 2a and 3d. The second recess 308 has a shape similar to the shape of the wedge 304 such that the wedge 304 can be matingly received within the second recess 308 and help to secure the keyboard 101 in the stored position.

FIGS. 3a-3d schematically illustrate the keyboard 101 being moved from the deployed position to the stored position. Only one track 202, link 206, sliding element 204, and pair of fasteners 208 are described below with reference to FIGS. 3a-3d. However, it should be understood that the same movements occur with respect to the second track 202, link 206, sliding element 204, and pair of fasteners 208.

Figure 3A:
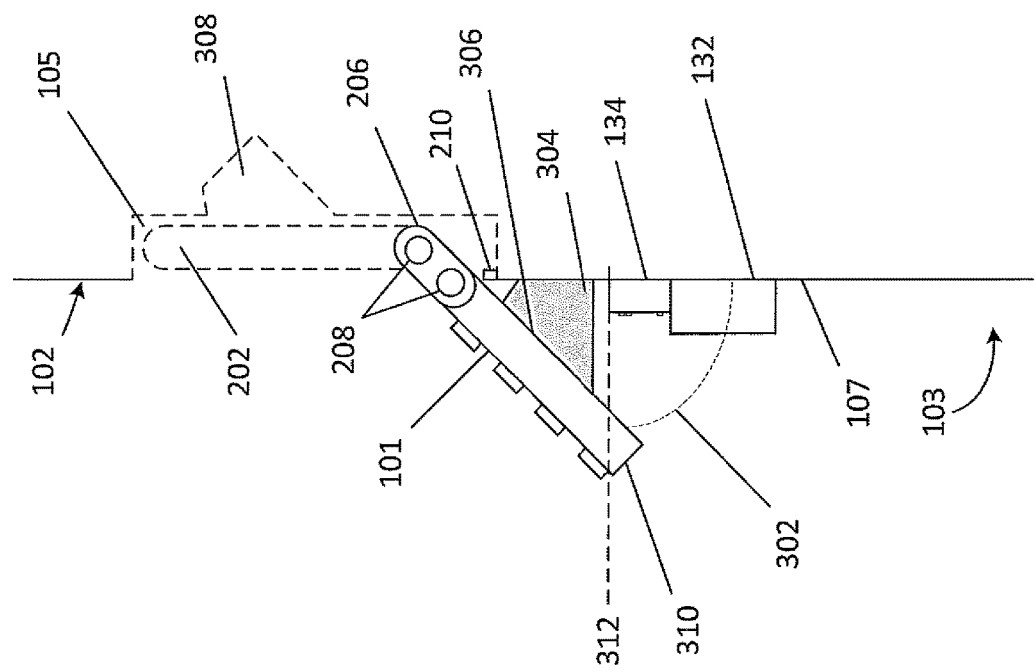
FIGS. 3a-3d are a series of side schematic views of a portion of the hemodialysis system of FIG. 1 showing the keyboard moving from the deployed position to the stored position.

Referring to FIG. 3a, when the keyboard 101 is in the deployed position, the keyboard 101 is disposed outside of the recess 105 at a particular angle 302 relative to the front surface 107 of the housing 103. The particular angle 302 may be between 10° and 80°, but is typically between 30° and 60°. The support member or wedge 304 is affixed to an undersurface 306 of the keyboard. When the keyboard 101 is in the deployed position, the wedge 304 makes contact with the front surface 107 of the housing 103. The dimensions of the wedge 304 can determine the particular angle 302 of the keyboard 101 relative to the front surface 107 of the housing 103 when the keyboard 101 is in the deployed position. For example, a wedge having a relatively small size results in the keyboard 101 being disposed at a relatively small angle relative to the front surface 107 of the housing 103, and a wedge having a relatively large size results in the keyboard 101 being disposed at a relatively large angle relative to the front surface 107 of the housing 103. The wedge 304 can have dimensions such that the keyboard is disposed at an angle of 30° and 60° relative to the front surface 107 of the housing 103 when the keyboard 101 is in the deployed position.

Figure 3B:
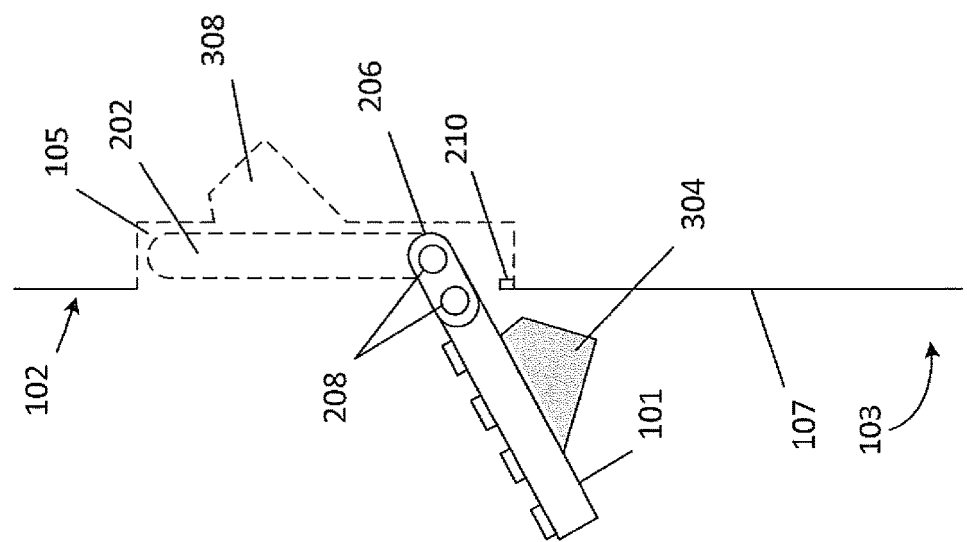
Figure 3C:
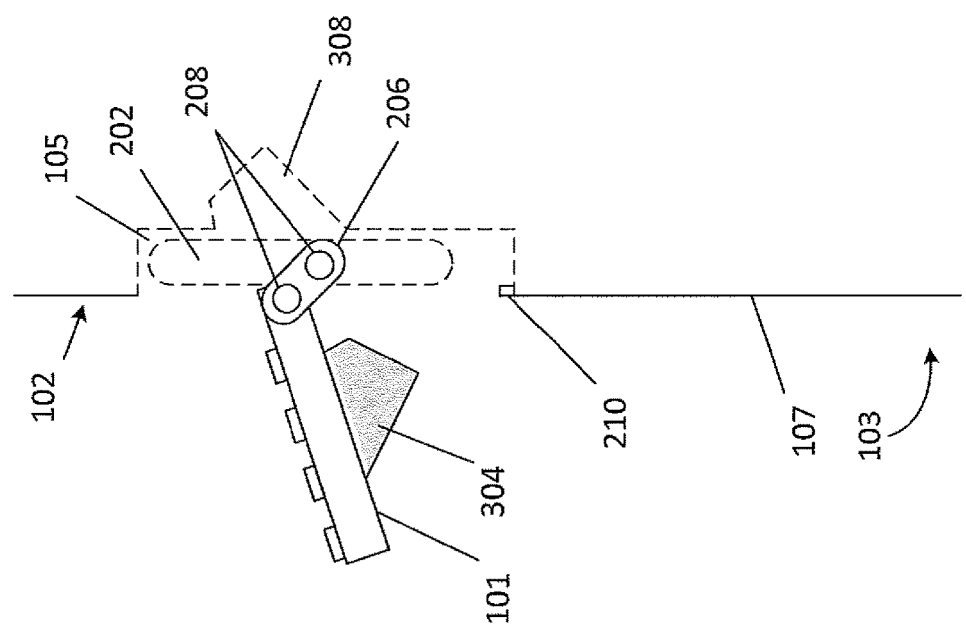
Figure 3D:
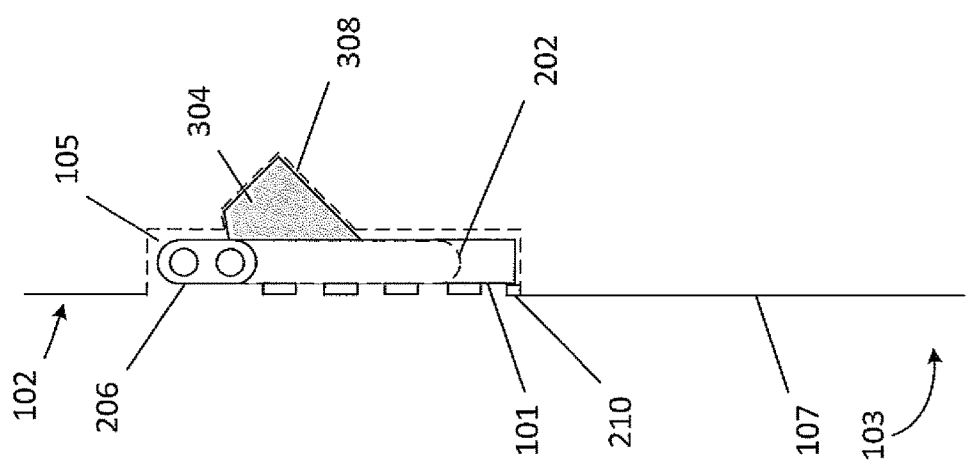

When the keyboard 101 is extended out from the hemodialysis machine 102 in the deployed position, as shown in FIG. 3a, the keyboard 101 may obstruct components that are disposed beneath the keyboard 101, such as the blood pump 132 and the blood pump module 134, from view from certain perspectives. For example, if a nurse is inputting information into the hemodialysis machine 102 via the keyboard 101 in the deployed position, the nurse's head is typically above the keyboard 101 and close to a vertical plane that extends from a bottom end 310 of the keyboard 101. From this perspective and other similar perspectives, the blood pump 132 and the blood pump module 134 would be obstructed from the nurse's view. This occurs partially because the bottom end 310 of the keyboard 101 is positioned further away from the front surface 107 of the housing 103 than the blood pump 132 and the blood pump module 134 when the keyboard 101 is in the deployed position, and the bottom end 310 of the keyboard 101 is positioned below a horizontal plane 312 that extends from the most vertical point of the blood pump 132 and the blood pump module 134 when the keyboard 101 is in the deployed position. While the keyboard 101 partially obstructs the user's view of certain components on the face of the hemodialysis machine 102 when the keyboard is in the deployed position, it is beneficial for the user to be able to view all components on the face of the hemodialysis machine 102 during treatment. For this reason, the keyboard 101 can be moved from the deployed position to the stored position, as illustrated in FIGS. 3b-3d. The user is provided with greater visibility of the various components on the face of the hemodialysis machine 102 when the keyboard 101 is in the stored position.

In FIG. 3b, the keyboard 101 and the link 206 that is affixed to the top end of the keyboard 101 are pivoted away from the front surface 107 of the housing 103. The keyboard 101 and the link 206 pivot about the fastener 208 that affixes the link 206 to the sliding element 204 (shown in FIGS. 2a and 2b) in the track 202.

In FIG. 3c, the link 206 continues to pivot about the fastener 208 that affixes the link 206 to the sliding element in the track 202. The link 206 also begins to pivot towards the keyboard 101 about the fastener 208 that affixes the link 206 to the top end of the keyboard 101. As a result, the keyboard 101 begins to pivot back towards the front surface 107 of the housing 103. After or as the pivoting occurs, the keyboard 101, the link 206, and the sliding element move upwards along the track 202.

In FIG. 3d, the link 206 continues to pivot about the fastener 208 that affixes the link 206 to the sliding element in the track 202. The link 206 also continues to pivot towards the keyboard 101 about the fastener 208 that affixes the link 206 to the top end of the keyboard 101. As a result, the keyboard 101 continues to pivot back towards the front surface 107 of the housing 103. As the pivoting occurs, the keyboard 101, the link 206, and the sliding element continue to move upwards along the track 202. The pivoting and the sliding occur until the keyboard 101 is in the stored position. When the keyboard 101 is in the stored position, the keyboard 101 is at least partially disposed in the recess 105, the wedge 304 is at least partially disposed in the second recess 308, and the link 206 is substantially vertical, having inverted during the keyboard's 101 move from the deployed position to the stored position. The keyboard 101 is in a substantially vertical position. The protrusion 210 retains the keyboard 101 in the stored position. The wedge 304 and the recess 308 also cooperate to help maintain the keyboard 101 in the stored position. When the keyboard 101 is in the stored position, the keys of the keyboard 101 are exposed for use by a user.

A method of using the hemodialysis system 100 to administer a dialysis treatment to a patient will now be described.

Before treatment begins, a nurse moves the keyboard 101 from the stored position (shown in FIGS. 1 and 2a) to the deployed position (shown in FIGS. 2b and 3a). The nurse enters information into the hemodialysis machine 102 via the keyboard 101. The keyboard 101 is disposed at an angle of 10° to 80° relative to the front surface 107 of the housing 103 of the hemodialysis machine 102. More particularly, the keyboard 101 is disposed at an angle of 30° and 60° relative to the front surface 107 of the housing 103 of the hemodialysis machine 102. Because the nurse is typically required to enter a large amount of information into the hemodialysis machine at this point, the keyboard 101 is positioned at a height and angle that allows the nurse to type comfortably.

The nurse typically begins by entering patient parameters into the keyboard 101 of the hemodialysis machine 102, such as a Patient ID. The nurse also enters medical treatment information, such as information related to the patient's treatment prescription. The information related to the patient's treatment prescription can include dialysate parameters and a concentrate selection. The treatment prescription can be analyzed by the hemodialysis machine 102 to determine appropriate operating parameters for the patient's treatment.

Once the patient parameters and the medical treatment information are entered into the hemodialysis machine 102, the keyboard 101 is positioned into the stored position (shown in FIGS. 1 and 2a). When the keyboard 101 is in the stored position, the keyboard is at least partially disposed in the recess 105 defined by the housing 103 of the hemodialysis machine 102. The keys of the keyboard 101 are exposed for use by the nurse when the keyboard 101 is in the stored position.

Once the keyboard 101 is in the stored position, the nurse prepares the patient for dialysis treatment. Referring back to FIG. 1, the arterial and venous patient lines 106, 108 are connected to the patient, and hemodialysis is initiated. During hemodialysis, blood is circulated through the blood circuit (i.e., the various blood lines and blood components, including the dialyzer 110, of the blood component set 104). At the same time, dialysate is circulated through the dialysate circuit (i.e., the various dialysate lines and dialysate components, including the dialyzer 110).

During hemodialysis, the blood pump 132 is activated causing blood to circulate through the blood circuit. The blood is drawn from the patient via the arterial patient line 106 and flows to an arterial pressure sensor capsule. An arterial pressure sensor on the front face of the module 130 aligns with the pressure sensor capsule and measures the pressure of the blood flowing through the blood circuit on the arterial side. The blood then flows through a pump line, which is operatively engaged with the blood pump 132. From the pump line, the blood flows to the dialyzer 110. After exiting the dialyzer 110, the blood flows through a venous pressure sensor capsule where the pressure of the blood on the venous side is measured by an associated pressure sensor on the front face of the module 130.

Upon reviewing the arterial and venous pressure measurements, the nurse may determine that the blood flow rate needs to be adjusted. The blood flow rate can be adjusted by changing the speed of the blood pump 132. The nurse looks at the display of the blood pump module 134 to view the blood flow rate setting of the blood pump 132. At this point of treatment, the keyboard 101 is in the stored position, so the nurse has an unobstructed view of the blood pump 132 and the blood pump module 134. The nurse can use the up and down keys of the blood pump module 134 to increase or decrease the speed of the blood pump 132, thereby increasing or decreasing the blood flow rate. Under some circumstances, the nurse can press the start/stop key to stop the blood pump 132. Because the keyboard 101 does not obstruct the user's view of the blood pump module 134 when it is in the stored position during treatment, this pump speed adjustment can be carried out quickly and efficiently.

During administration of the dialysis treatment, the nurse may enter information into the hemodialysis machine 102 via the keyboard 101 while the keyboard 101 is in the stored position. For example, after looking at the display of the blood pump module 134 to view the blood flow rate setting of the blood pump 132, the nurse may determine that certain treatment parameters for the hemodialysis machine 102 need to be adjusted. The nurse may, for example, determine that the blood flow rate setting requires the ultrafiltration rate to be adjusted. The nurse can adjust the ultrafiltration rate of the hemodialysis machine 102 using the keyboard 101 while the keyboard 101 is in the stored position. Many nurses may find it easiest to input small amounts of data like this via the keyboard 101 while the keyboard 101 is in the stored position, rather than moving the keyboard 101 to the deployed position. The ability of the nurse to input data while the keyboard 101 is in the stored position may, therefore, increase the speed with which the treatment can be carried out.

Once dialysis treatment has concluded, the nurse can move the keyboard 101 back into the deployed position.

While certain implementations have been described, other implementations are possible.

While the hemodialysis machine 102 has been described as including multiple tracks 202, links 206, sliding elements 204, and pairs of fasteners 208, in some implementations, the hemodialysis machine includes only one track, link, sliding element, and pair of fasteners.

While one example of a mechanism configured to permit the keyboard to move between stored and deployed positions has been described, other types of mechanisms can be used.

Figure 5A:
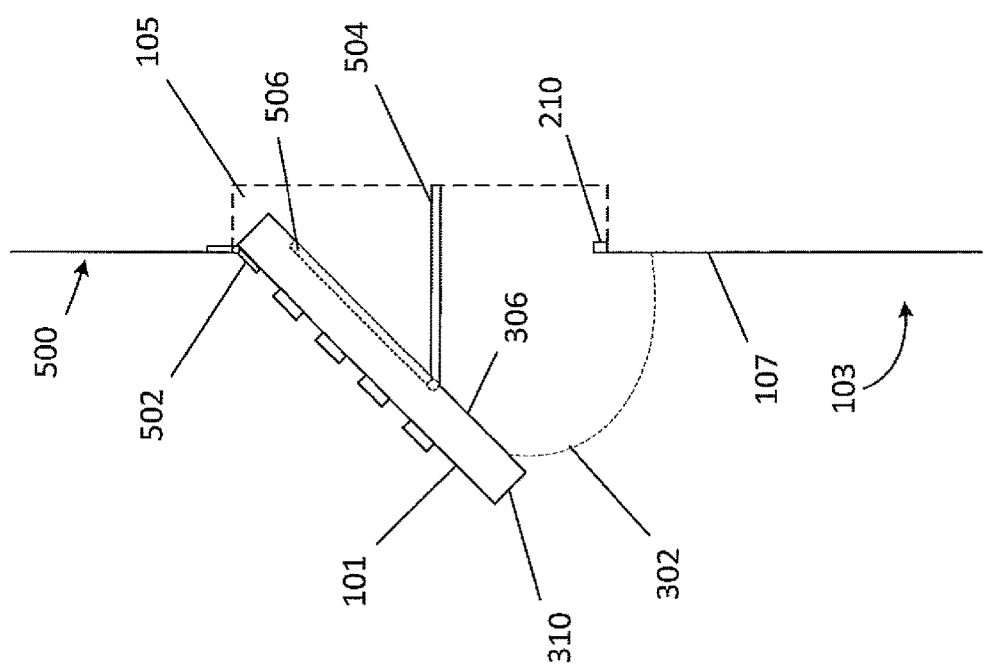
FIG. 5a is a side schematic view of a portion of a hemodialysis system and an alternative implementation of a keyboard in which the keyboard is connected to a housing of the hemodialysis machine by a hinge.
Figure 5B:
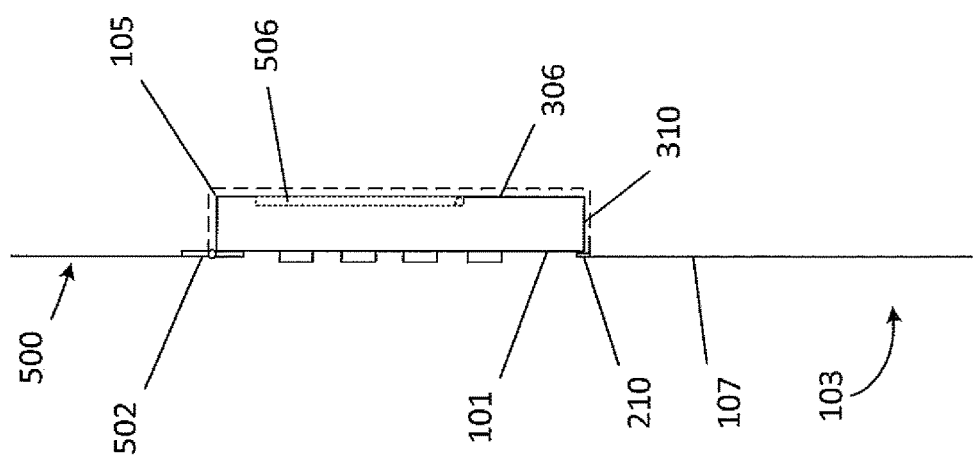
FIG. 5b is a side schematic view of a portion of the hemodialysis system of FIG. 5a showing the keyboard in the stored position.

FIGS. 5a-5c show a series of side schematic views of a portion of the hemodialysis machine 102 that show an alternative mechanism for securing the keyboard 101 to the hemodialysis machine 102. These figures show the keyboard 101 moving from the deployed position to the stored position in which the link 206 does not invert.

Figure 4A:
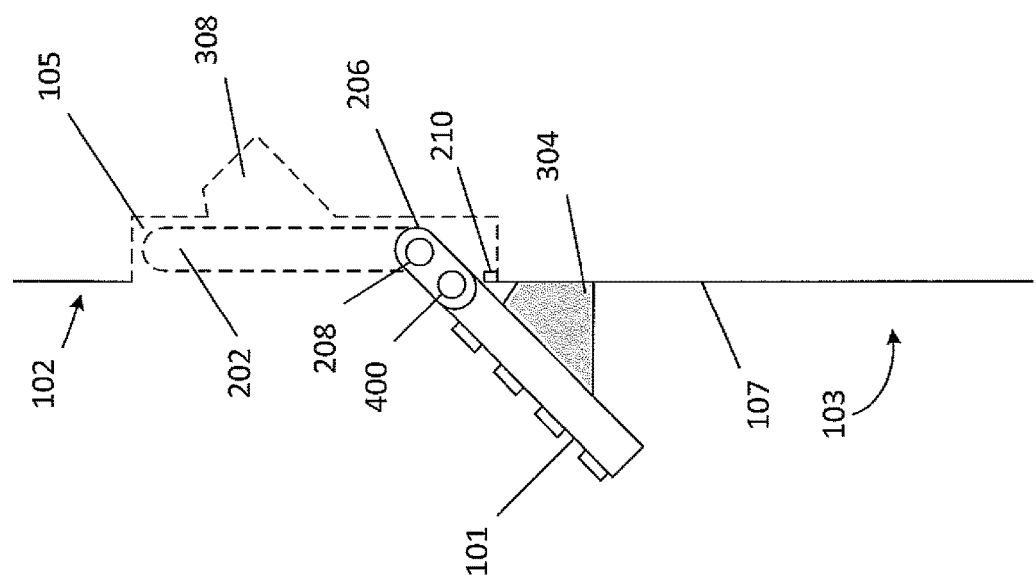
FIGS. 4a-4c are a series of side schematic views of a portion of a hemodialysis system showing an alternative implementation of a keyboard moving from the deployed position to the stored position.

In FIG. 4a, the keyboard 101 is in the deployed position. The link 206 is fixed to the top end of the keyboard 101 by a screw 400 that prevents the link 206 from pivoting about the screw 400.

Figure 4B:
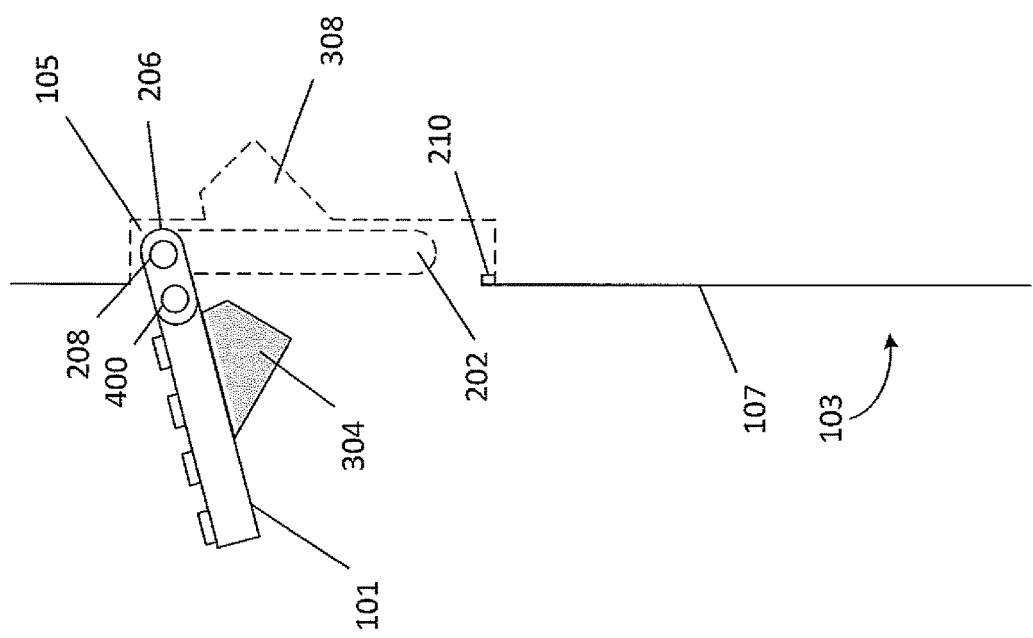

In FIG. 4b, the keyboard 101 and the link 206 that is affixed to the top end of the keyboard 101 are pivoted away from the front surface 107 of the housing 103. The keyboard 101 and the link 206 pivot about the fastener 208 that affixes the link 206 to the sliding element 204 in the track 202. The sliding element 204 is obstructed from view by the link 206, and is therefore not shown in FIG. 4b. After or as the pivoting occurs, the keyboard 101, the link 206, and the sliding element move upwards along the track 202 to the top of the track 202. Unlike the system shown in FIGS. 3a-3d, the link 206 does not pivot about the screw 400 that affixes the link 206 to the top end of the keyboard 101.

Figure 4C:
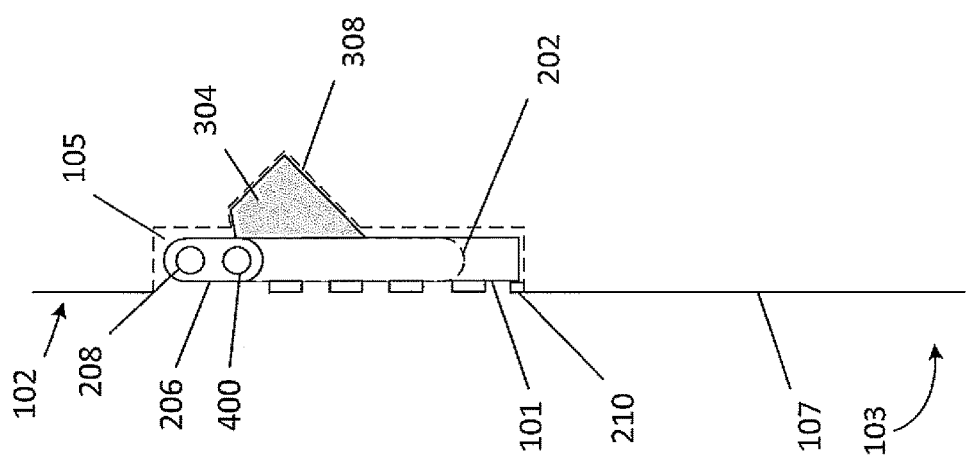

In FIG. 4c, the keyboard 101 pivots back towards the front surface 107 of the housing 103 until the keyboard 101 is in the stored position. When the keyboard 101 is in the stored position, the keyboard 101 is at least partially disposed in the recess 105, the wedge 304 is at least partially disposed in the second recess 308, and the link 206 is substantially vertical. Unlike the system shown in FIGS. 3a-3d, the link 206 does not invert during the keyboard's move from the deployed position to the stored position. The protrusion 210 retains the keyboard 101 in the stored position. When the keyboard 101 is in the stored position, the keys of the keyboard 101 are exposed for use.

FIG. 5a shows a side schematic view of a portion of a hemodialysis machine 500 and an alternative mechanism for securing the keyboard 101 to the hemodialysis machine 500. The keyboard 101 is connected to the housing 103 of the hemodialysis machine 500 by a hinge 502. When the keyboard 101 is in the deployed position, as shown in FIG. 5a, the keyboard 101 is disposed outside of the recess 105 at a particular angle 302 relative to the front surface 107 of the housing 103. The particular angle 302 may be between 10° and 80°, but is typically between 30° and 60°.

The hinge 502 has a first end that is affixed to the housing 103 above the recess 105 and a second end that is affixed to the top end of the keyboard. The keyboard 101 includes a support leg 502. A first end of the leg 504 is pivotably affixed to the undersurface 306 of the keyboard 101. The leg 504 is pivoted away from the undersurface 306 of the keyboard 101 from a recess 506 to assume an extended position. A second end of the leg 504 makes contact with a surface within the recess 105 when the keyboard 101 is in the deployed position and the leg 504 is in the extended position, thereby propping the keyboard 101 up against the surface within the recess 105. The leg 504 can include a locking mechanism for locking the leg 504 into the extended position.

The dimensions of the leg 504 can determine the particular angle 302 of the keyboard 101 relative to the front surface 107 of the housing 103 when the keyboard 101 is in the deployed position. For example, a leg 504 having a relatively short length results in the keyboard 101 being disposed at a relatively small angle relative to the front surface 107 of the housing 103, and a leg 504 having a relatively long length results in the keyboard 101 being disposed at a relatively large angle relative to the front surface 107 of the housing 103. The leg 504 can have dimensions such that the keyboard is disposed at an angle of 30° and 60° relative to the front surface 107 of the housing 103 when the keyboard 101 is in the deployed position.

FIG. 5b shows a side schematic view of a portion of the hemodialysis machine 500 that shows the keyboard 101 of FIG. 5a in the stored position. The leg 504 (shown in FIG. 5a) is stored in the recess 506 of the keyboard 101 when the keyboard 101 is in the stored position. The leg 504 is pivoted toward the undersurface 306 of the keyboard 101 into the recess 506 to assume a stored position. The keyboard 101 is pivoted towards the front surface 107 of the housing 103 until the keyboard 101 is in the stored position. When the keyboard 101 is in the stored position, the keyboard 101 is at least partially disposed in the recess 105. The keyboard 101 is in a substantially vertical position. The protrusion 210 retains the keyboard 101 in the stored position. When the keyboard 101 is in the stored position, the keys of the keyboard 101 are exposed for use by a user.

Figure 6:
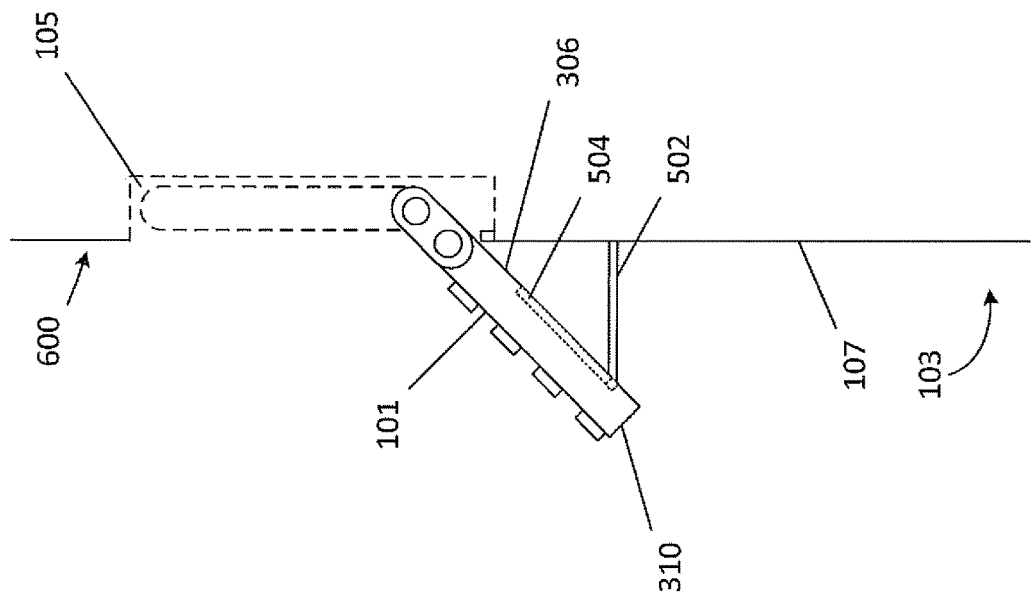
FIG. 6 is a side schematic view of a portion of a hemodialysis system and an alternative implementation of a keyboard in which the keyboard includes a support leg.

FIG. 6 shows a side schematic view of a portion of a hemodialysis machine 600 and an alternative mechanism for securing the keyboard 101 to the hemodialysis machine 600. Rather than including a wedge, the keyboard 101 includes a leg 502 having a first end that is pivotably affixed to the undersurface 306 of the keyboard 101. A second end of the leg 502 makes contact with the surface within the recess 105 when the keyboard 101 is in the deployed position and the leg 502 is in the extended position, thereby propping the keyboard 101 up against the surface within the recess 105. The leg 502 is stored in a recess 504 of the keyboard 101 when the keyboard 101 is in the stored position, much in the same manner as described with reference to FIGS. 5a and 5b.

While we have described a protrusion 210 affixed to the housing 103 that retains the keyboard 101 in the stored position, other mechanisms can be used to retain the keyboard in the stored position. In some implementations, the wedge can include one or more protrusions that mate with one or more cavities extending inwardly from the recess 308 when the keyboard 101 is in the stored position. When the protrusions are positioned into the cavities, the wedge is held in place in the second recess, thereby helping to retain the keyboard in the stored position.

While the hinge 500 has been described as being affixed to the housing 103 above the recess 105 of the hemodialysis machine 102, in some implementations, the first end of the hinge is affixed within the recess to a top surface of the recess.

While the first end of the leg 502 has been described as being pivotably affixed to the undersurface 306 of the keyboard 101, in some implementations, the second end of the leg is pivotably affixed to the undersurface of the keyboard, and the first end of the leg makes contact with the surface within the recess when the keyboard is in the deployed position and the leg is in the extended position, thereby propping the keyboard 101 up against the surface within the recess. In other words, the second end of the leg is pivotably affixed to the undersurface of the keyboard nearer to the bottom end of the keyboard than to the top end of the keyboard.

While the leg 502 has been shown as forming an angle of approximately 90° relative to the surface within the recess 105, in some implementations, the leg forms a different angle relative to the surface within the recess that results in the keyboard being disposed at an angle of 10° to 80° relative to the front surface of the housing.

While the keyboard 101 has been described as including one leg 502 and one recess 504, in some implementations, the keyboard includes more than one leg and more than one recess. For example, the keyboard can include a leg and a recess pair near each side of the keyboard (e.g., the right and left sides of the keyboard).

While we described the hemodialysis machine 102 as including a touch screen 118, in some implementations, the hemodialysis machine includes a traditional monitor.

While we have described the keyboard 101 being connected to a hemodialysis machine 102, the keyboard could alternatively be included in other types of medical treatment systems. Examples of other medical treatment systems in which the keyboard 101 can be used include hemofiltration systems, hemodiafiltration systems, apheresis systems, cardiopulmonary bypass systems, and peritoneal dialysis systems.

A number of implementations have been described. Nevertheless, it will be understood that various modifications may be made without departing from the spirit and scope of the invention. Accordingly, other implementations are within the scope of the following claims.

What is claimed is:

1. A medical treatment system comprising:
   a housing;
   a recess defined by the housing;
   a blood pump disposed on the front surface of the housing beneath the recess; and
   a keyboard connected to the housing by a mechanism configured to permit the keyboard to move between:
      a deployed position in which the keyboard is disposed outside of the recess at an angle of 10° to 80° relative to a front surface of the housing, wherein the keyboard at least partially obstructs a user's view of the blood pump when the keyboard is in the deployed position; and
      a stored position in which (i) the keyboard is at least partially disposed in the recess to allow for the user's unobstructed view of the blood pump and (ii) keys of the keyboard are exposed for use by a user,
   wherein the mechanism comprises a track that is disposed on the housing within the recess and is obstructed from view by the front surface of the housing, the track including a sliding element for moving along the track, wherein a top end of the keyboard is affixed to the sliding element such that the keyboard can move along the track in relation to the sliding element.

2. The medical treatment system of claim 1, wherein the medical treatment system is a hemodialysis system that includes a hemodialysis machine.

3. The medical treatment system of claim 1, wherein the keyboard is in a substantially vertical position when the keyboard is disposed in the recess.

4. The medical treatment system of claim 1, wherein a bottom end of the keyboard is positioned further away from the front surface of the housing than the blood pump when the keyboard is in the deployed position.

5. The medical treatment system of claim 1, wherein the mechanism comprises:
a link having a first end that is affixed to the sliding element of the track,
wherein a top end of the keyboard is affixed to a second end of the link such that the keyboard can move along the track in relation to the sliding element.

6. The medical treatment system of claim 1, further comprising:
a support member that is affixed to an undersurface of the keyboard, wherein the support member makes contact with the recess to retain the keyboard at the angle of 10° to 80° relative to the front surface of the housing when the keyboard is in the deployed position.

7. The medical treatment system of claim 6, wherein the dimensions of the support member result in the keyboard being disposed at an angle of 30° to 60° relative to the front surface of the housing when the keyboard is in the deployed position.

8. The medical treatment system of claim 6, wherein the support member is a wedge.

9. The medical treatment system of claim 1, further comprising:
a protrusion that is affixed to the housing adjacent the recess, wherein the protrusion retains the keyboard within the recess when the keyboard in the stored position.

10. The medical treatment system of claim 5, wherein a bottom end of the keyboard is positioned below a horizontal plane that extends from the most vertical point of the blood pump when the keyboard is in the deployed position.

11. The medical treatment system of claim 1, further comprising:
a hinge having a first end that is affixed to the housing, wherein a top end of the keyboard is affixed to a second end of the hinge; and
a leg having a first end that is pivotably affixed to an undersurface of the keyboard, wherein a second end of the leg makes contact with a surface within the recess when the keyboard is in the deployed position and the leg is in an extended position.

12. The medical treatment system of claim 11, wherein the keyboard is disposed at an angle of 30° to 60° relative to the front surface of the housing when the keyboard is in the deployed position and the leg is in the extended position.

13. The medical treatment system of claim 1, wherein the keyboard is disposed outside of the recess at an angle of between 30° and 60° relative to the front surface of the housing when the keyboard is in the deployed position.

* * * * *